United States Patent
Ridinger et al.

(10) Patent No.: US 7,094,917 B2
(45) Date of Patent: Aug. 22, 2006

(54) PROCESSES FOR REFINING COMPOSITIONS CONTAINING DIALKYL CARBONATES

(75) Inventors: Richard Ridinger, Monheim (DE); Levent Yueksel, Duesseldorf (DE); Georg Fieg, Mettmann (DE)

(73) Assignee: Cognis Deutschland GmbH & Co., KG, Duesseldorf (DE)

( * ) Notice: Subject to any disclaimer, the term of this patent is extended or adjusted under 35 U.S.C. 154(b) by 0 days.

(21) Appl. No.: 10/487,615

(22) PCT Filed: Aug. 13, 2002

(86) PCT No.: PCT/EP02/09042

§ 371 (c)(1),
(2), (4) Date: Feb. 23, 2004

(87) PCT Pub. No.: WO03/018527

PCT Pub. Date: Mar. 6, 2003

(65) Prior Publication Data

US 2004/0242914 A1    Dec. 2, 2004

(30) Foreign Application Priority Data

Aug. 21, 2001  (DE) .................... 101 40 846

(51) Int. Cl.
*C07C 69/96*    (2006.01)
(52) U.S. Cl. ...................... 558/277; 558/274
(58) Field of Classification Search ........... 558/277, 558/274
See application file for complete search history.

(56) References Cited

U.S. PATENT DOCUMENTS

| | | | |
|---|---|---|---|
| 2,687,425 A * | 8/1954 | Douthitt ................... 558/277 |
| 3,627,810 A * | 12/1971 | Chang ..................... 558/276 |
| 4,307,032 A * | 12/1981 | Krimm et al. ............. 558/277 |
| 4,348,536 A * | 9/1982 | Blahak et al. ............. 560/169 |
| 4,390,463 A * | 6/1983 | Boden et al. ............. 512/18 |
| 4,394,221 A * | 7/1983 | Stage et al. ............... 203/89 |
| 4,436,668 A * | 3/1984 | Harder et al. ............. 558/260 |
| 4,599,143 A * | 7/1986 | Stage ....................... 203/6 |
| 4,655,879 A * | 4/1987 | Brockmann et al. ....... 203/37 |
| 4,691,041 A * | 9/1987 | Duranleau et al. ........ 558/277 |
| 4,810,330 A * | 3/1989 | Stage ....................... 203/4 |
| 4,838,997 A * | 6/1989 | Merk ....................... 554/205 |
| 5,009,803 A * | 4/1991 | Brandolese ............... 508/462 |
| 5,076,896 A * | 12/1991 | Carduck et al. .......... 203/41 |
| 5,132,447 A * | 7/1992 | King, Jr. .................. 558/274 |
| 5,231,212 A * | 7/1993 | Buysch et al. ............ 558/277 |
| 5,266,716 A * | 11/1993 | Buysch et al. ............ 558/260 |
| 5,292,917 A * | 3/1994 | Nishihira et al. .......... 558/277 |
| 5,338,878 A * | 8/1994 | Pacheco et al. ........... 558/277 |
| 5,359,118 A * | 10/1994 | Wagner et al. ............ 558/277 |
| 5,387,374 A * | 2/1995 | Westfechtel et al. ...... 508/462 |
| 5,489,703 A * | 2/1996 | Pacheco et al. ........... 558/277 |
| 5,543,548 A * | 8/1996 | Landscheidt et al. ...... 558/277 |
| 5,625,091 A * | 4/1997 | Buysch et al. ............ 558/274 |
| 5,653,966 A * | 8/1997 | Bertoli et al. ............. 424/69 |
| 5,731,453 A * | 3/1998 | Nishihira et al. .......... 558/274 |
| 5,834,275 A * | 11/1998 | Raehse et al. ............. 435/183 |
| 5,834,615 A * | 11/1998 | Nishihira et al. .......... 558/274 |
| 5,986,125 A * | 11/1999 | Reuter et al. .............. 558/277 |
| 6,093,842 A * | 7/2000 | Oyevaar et al. ........... 558/274 |
| 6,384,262 B1 * | 5/2002 | Ofori et al. ................ 558/274 |
| 6,420,589 B1 * | 7/2002 | Ofori et al. ................ 558/274 |
| 2001/0051740 A1 * | 12/2001 | Mizukami et al. ......... 558/260 |

FOREIGN PATENT DOCUMENTS

| | | | |
|---|---|---|---|
| EP | 0 089 709 A1 | | 9/1983 |
| EP | 0 393 749 B1 | | 10/1990 |
| GB | 2176713 A | * | 1/1987 |
| WO | WO 9729170 A1 | * | 8/1997 |
| WO | WO 97/47583 | | 12/1997 |

OTHER PUBLICATIONS

March, J., Advanced Organic Chemistry, 4th ed., Wiley & Sons, New York (1992), at p. 397, Reaction 0-23 ("Alcoholysis of Carboxylic Esters. Transesterification").*

* cited by examiner

*Primary Examiner*—Deborah C. Lambkin
(74) *Attorney, Agent, or Firm*—John F. Daniels; Jane E. Alexander

(57) ABSTRACT

Processes for refining dialkyl carbonate-containing compositions are described, wherein a composition comprising a dialkyl carbonate is provided; and the composition is subjected to a rectification wherein low-boiling impurities are removed, and a rectification wherein high-boiling impurities are removed; and subsequently to a deodorization wherein medium-boiling impurities are removed.

15 Claims, 1 Drawing Sheet

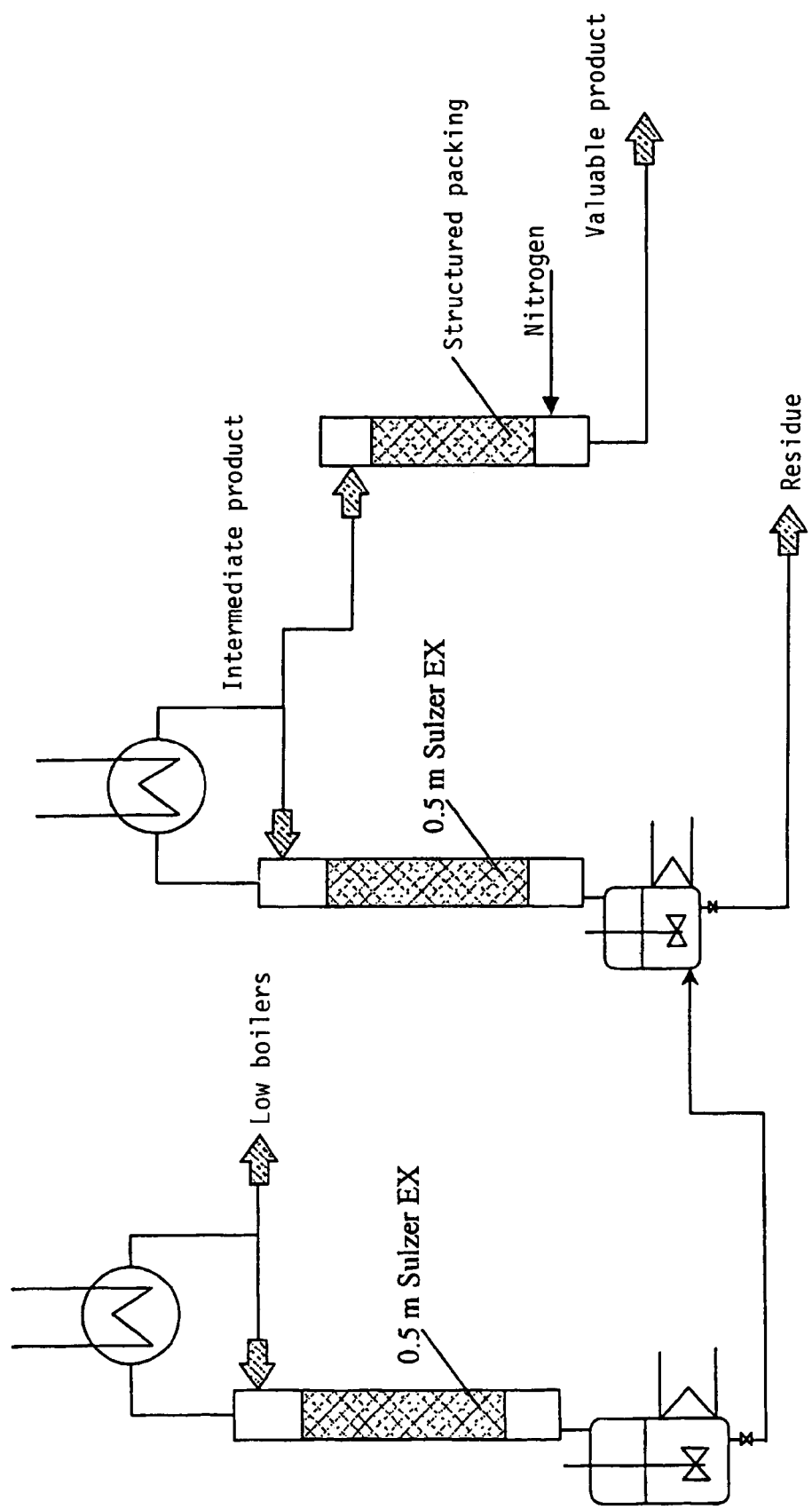

PROCESSES FOR REFINING COMPOSITIONS CONTAINING DIALKYL CARBONATES

BACKGROUND OF THE INVENTION

Dialkyl carbonates are interesting new oil components for cosmetic products and are normally obtained by transesterification of dimethyl or diethyl carbonate with relatively long-chain fatty alcohols. Particular preference attaches to the production and use of dioctyl carbonate which is commercially available under the INCI name of Dicaprylyl Carbonate and the registered name of Cetiol® CC (Cognis Deutschland GmbH) [cf. WO 97/47583 (Cognis)]. Unfortunately, carbonates have the disadvantage of a "sweaty" odor so that perfuming is necessary where they are used in cosmetic products. The deodorization with steam normally applied in such cases has proved unsuccessful.

Accordingly, the problem addressed by the present invention was to provide dialkyl carbonates which would have an improved odor quality in relation to the prior art and which would therefore be suitable for use in cosmetic products.

BRIEF SUMMARY OF THE INVENTION

The present invention relates, in general, to the field of cosmetics and, more particularly, to a process for the production of oil components of the dialkyl carbonate type, in which products with improved odor properties are obtained.

The present invention relates to a process for the production of dialkyl carbonates corresponding to formula (I):

$$R^1OCOOR^2 \quad (I)$$

in which $R^1$ and $R^2$ independently of one another represent linear or branched hydrocarbon radicals containing 6 to 22 carbon atoms and 0 or 1 to 3 double bonds, by transesterification of $C_{1-4}$ dialkyl carbonates with $C_{6-22}$ alcohols, characterized in that (a) the crude transesterification mixture is subjected to a first rectification in which the low-boiling impurities are distilled off,
(b) the "bottom" product thus obtained is subjected to a second rectification in which the high-boiling impurities are removed and
(c) finally, in a deodorizing column, the distillate thus obtained is freed from medium-boiling impurities, more particularly odor carriers, either with steam or with inert gases.

The invention is based on the observation that the odor problem with dialkyl carbonates is attributable to very different impurities which can only be removed by different process measures. It has surprisingly been found that the combination of two rectification steps and one deodorization step ultimately yields a product which is satisfactory from the odor perspective and which may be used without additional perfuming in cosmetic products.

DETAILED DESCRIPTION OF THE INVENTION

Rectification

In the course of the two-stage rectification, the unwanted low-boiling impurities are removed in the first step. The bottom product is then subjected to a second rectification in which the high-boiling impurities are left in the bottom of the column and only the distillate is subsequently used. It has proved to be particularly advantageous—because less damage is done to the materials used—to evaporate the crude transesterification mixture and/or the distillate obtained as intermediate product in a combination of thin-layer and falling-film evaporators. The rectification itself is carried out in particular in columns with structured packings which preferably have a pressure loss of less than 1–2 mbar/m. The first rectification is normally carried out at temperatures (bottom) in the range from 180 to 250° C. and under a reduced pressure (head) of 0.01 to 10 mbar and preferably at temperatures (bottom) in the range from 180 to 200° C. and under a reduced pressure (head) of 1 to 10 mbar. The second rectification is normally carried out at temperatures (bottom) in the range from 150 to 250° C. and under a reduced pressure (head) of 0.01 to 0.5 mbar and preferably at temperatures (bottom) in the range from 150 to 180° C. and under a reduced pressure (head) of 0.01 to 0.5 mbar.

Deodorization

The deodorization is generally carried out in a column under a reduced pressure of 10 to 100 mbar using either steam or inert gases, preferably nitrogen.

EXAMPLE

The working up of a technical dioctyl carbonate was carried out in two coupled rectifying columns each with a 0.5 m EX packing (Sulzer AG) and a deodorizing column. The column diameters were 30 mm. The crude transesterification mixture was evaporated in a combination of thin-layer and falling-film evaporators and delivered to the first rectifying column where the head pressure was 5 mbar, the bottom temperature 185° C., the pressure loss ca. 9 mbar and the reflux ratio 5. 43.5% by weight low-boiling distillate and 56.5% by weight valuable product were obtained at the bottom of the column. The bottom product was then evaporated in the same way and delivered to the second rectifying column where the head pressure was 0.1 mbar, the bottom temperature 176° C., the pressure loss ca. 9 mbar and the reflux ratio 3. The subsequent deodorization was carried out with nitrogen at 100° C. in a separate column. The product obtained was completely odorless, even after storage for 6 months.

FIG. 1 is a flow chart of the process.

The invention claimed is:

1. A process comprising the steps of:
   (a) providing a composition comprising a dialkyl carbonate formed by transesterification of a $C_{1-4}$ dialkyl carbonate with a $C_{6-22}$ alcohol;
   (b) subjecting the composition to a rectification wherein low-boiling impurities are removed an a bottom product remains;
   (c) subjecting the bottom product to a rectification wherein high-boiling impurities are removed and a destillate remains; and subsequently
   (d) subjecting the distillate to a deodorization wherein medium-boiling impuritips are removed.

2. The process according to claim 1, wherein the dialkyl carbonate is of the general formula (I):

$$R^1OC(O))OR^2 \quad (I)$$

wherein $R^1$ and $R^2$ each independently represent a linear or branched hydrocarbon radical having from 6 to 22 carbon atoms and up to three carbon-carbon double bonds.

3. The process according to claim 1, wherein the rectification wherein low-boiling impurities are removed comprises evaporation of the composition in a combination of a thin-layer evaporator and a falling film evaporator.

4. The process according to claim 1, wherein the rectification wherein high-boiling impurities are removed comprises evaporation of the composition in a combination of a thin-layer evaporator and a falling film evaporator.

5. The process according to claim 1, wherein the rectification wherein low-boiling impurities are removed comprises evaporation of the composition in a combination of a thin-layer evaporator and a falling film evaporator; and wherein the rectification wherein high-boiling impurities are removed comprises evaporation of the composition in a combination of a thin-layer evaporator and a falling film evaporator.

6. The process according to claim 1, wherein the rectification wherein low-boiling impurities are removed is carded out in a column comprising structured packings.

7. The process according to claim 1, wherein the rectification wherein high-boiling impurities are removed is carried out in a column comprising structured packings.

8. The process according to claim 6, wherein the column comprising structured packings has a pressure loss of less than 2 mbar/m.

9. The process according to claim 7, wherein the column comprising structured packings has a pressure loss of less than 2 mbar/m.

10. The process according to claim 1, wherein the rectification wherein low-boiling impurities are removed is carried out at a temperature of from 180 to 250° C. and at a pressure of from 0.01 to 10 mbar.

11. The process according to claim 1, wherein the rectification wherein high-boiling impurities are removed is carded out at a temperature of from 150 to 250° C. and at a pressure of from 0.01 to 0.5 mbar.

12. The process according to claim 1, wherein the deodorization is carried out using a gas selected from the group consisting of steam and inert gases.

13. The process according to claim 1, wherein the deodorization is carried out at a pressure of from 10 to 100 mbar.

14. A process comprising the steps of:
  (a) providing a composition comprising a dialkyl carbonate reaction product mixture prepared by transesterification of a $C_{1-4}$ dialkyl carbonate with a $C_{6-22}$ alcohol;
  (b) subjecting the composition to a first rectification carried out at a temperature of from 180 to 250° C. and at a pressure of from 0.01 to 10 mbar wherein low-boiling impurities are removed and a bottom product remains,
  (c) subjecting the bottom product to a second rectification carried out at a temperature of from 150 to 250° C. and at a pressure of from 0.01 to 0.5 mbar wherein high-boiling impurities are removed and a distillate remains; and subsequently
  (d) subjecting the distillate to a deodorization carried out in a column under a pressure of from 10 to 100 mbar wherein medium-boiling impurities are removed with a gas selected from the group consisting of steam and inert gases.

15. The process according to claim 14, wherein the first rectification comprises evaporation of the composition in a combination of a thin-layer evaporator and a falling film evaporator and wherein the second rectification comprises evaporation of the composition in a combination of a thin-layer evaporator and a falling film evaporator.

* * * * *